United States Patent [19]

Johnson

[11] 4,022,198

[45] May 10, 1977

[54] INTRAUTERINE DEVICE REMOVER

[75] Inventor: Neil Arthur Johnson, Sunnyvale, Calif.

[73] Assignee: Alza Corporation, Palo Alto, Calif.

[22] Filed: Apr. 16, 1976

[21] Appl. No.: 677,762

[52] U.S. Cl. .................................. 128/130
[51] Int. Cl.$^2$ .......................... A61F 5/46
[58] Field of Search .......... 128/127, 130, 263, 260, 128/330

[56] References Cited

UNITED STATES PATENTS

| 3,635,215 | 1/1972 | Shea et al. | 128/130 |
| 3,635,222 | 1/1972 | Robinson | 128/130 X |
| 3,786,808 | 1/1974 | Lerner | 128/130 |

Primary Examiner—Lawrence W. Trapp

Attorney, Agent, or Firm—Thomas E. Ciotti; Paul L. Sabatine; Edward L. Mandell

[57] ABSTRACT

An apparatus for nonsurgically removing certain IUDs, such as 7- or T-shaped IUDs, from within the uterus via the cervical canal. The apparatus is composed of: a rod-shaped handle; a tube, one end of which slidably fits over one end of the handle such that the handle may slide within the tube from a first position to a second position; a hole in the other end of the tube; and a filament that extends between and is attached to the other end of the handle and the other end of the tube via the hole. The filament is wrapped snugly about the other end of the tube when the handle is slid to its first position and the filament defines an outwardly extending loop when the handle is slid to its second position, which loop is used to entrap the IUD.

8 Claims, 4 Drawing Figures

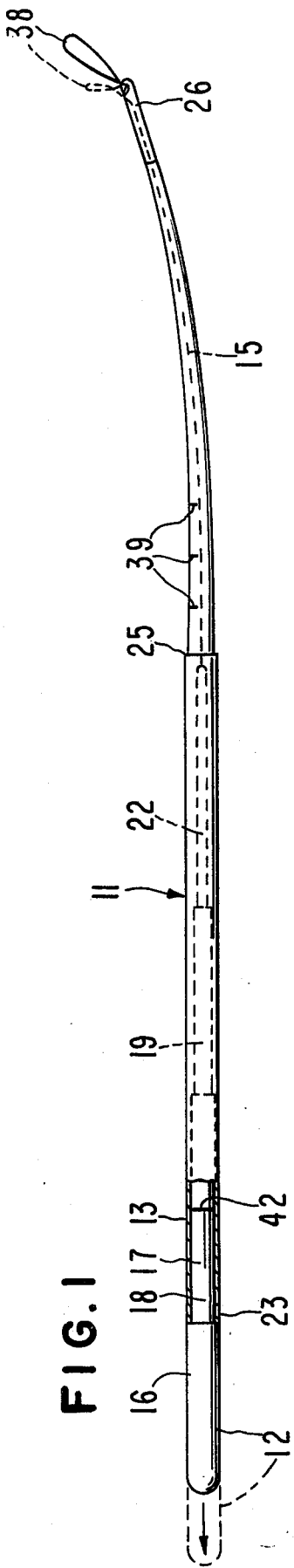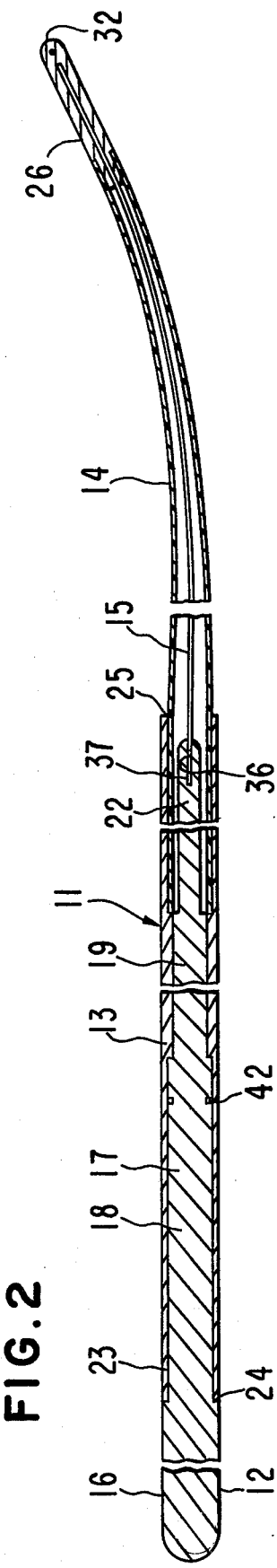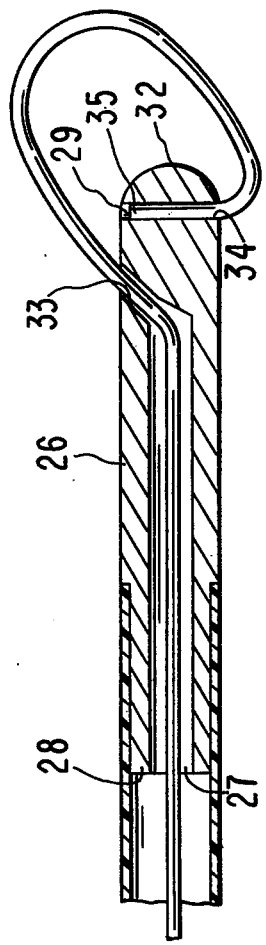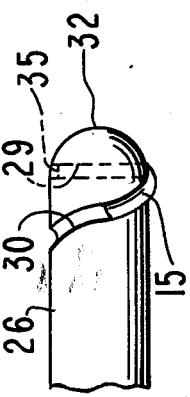

INTRAUTERINE DEVICE REMOVER

BACKGROUND OF THE INVENTION

1. Field of the Invention

The invention relates to a medical apparatus for removing an IUD from within a uterus via the cervical canal without surgery.

2. Description of the Prior Art

The most common device used to nonsurgically remove an IUD from within a uterus via the cervical canal consists of a string (strings, or string-like appendage(s)) that is attached to the IUD before the IUD is inserted and trails from the IUD through the cervical canal into the vagina when the IUD is emplaced. The IUD is removed by simply gripping the string and pulling it. However, such devices sometimes become unattached from the IUD during wearing or work their way into the cervical canal or uterus so that they are not exposed to the physician. In other instances they may weaken and break when they are pulled on during the removal procedure.

U.S. Pat. No. 3,635,215 describes an apparatus for removing an IUD from within a uterus via the cervical canal without surgery. The patented apparatus basically consists of an elongated rod with a handle at one end and a hood at the other end and a tube that fits slidably over the rod such that the hood grips the edge of the tube when the rod is slid to its rearwardmost position. This apparatus is inserted through the cervical canal into the uterus and its hook is hooked over the IUD. The snagged IUD is then drawn tightly between the hook and the tube by sliding the rod rearwardly. The problem with the patented apparatus is that its hook is essentially capable of hooking only IUD segments or appendages that are rigid and lie transfundally within the uterus.

SUMMARY OF THE INVENTION

The invention is an apparatus for removing certain IUDs from within a uterus via the cervical canal. IUDs that may be removed with the apparatus have an appendage that lies generally longitudinally within the uterus (and perhaps cervical canal). Such IUDs include the "Tatum T" (see U.S. Pat. No. 3,533,406), the "PROGESTASERT" system (see U.S. Pat. No. 3,896,819), and the "Copper 7" (see U.S. Pat. No. 3,777,748).

The apparatus comprises: a rod shaped handle; a hollow elongated tube or barrel, one end of which fits over one end of the handle such that the handle is slidable axially within the tube from a first position to a second position; a hole through the side of the hollow tube at the other end of the hollow tube; and a filament extending from said other end of the tube through the hole to the said one end of the handle, one end of the filament being attached to the side of the tube at a position above and generally opposite the hole and the other end of the filament being attached to said one end of the handle, the filament being wrapped about said other end of the tube when the handle is in said first position and defining a loop of predetermined size that extends outwardly from said other end of the hollow tube when the handle is in its second position, the size of the loop being adjustable by sliding the handle between said first and second positions.

BRIEF DESCRIPTION OF THE DRAWINGS

In the drawings:

FIG. 1 is a side elevational view, partly in section, of the preferred embodiment of the IUD remover of the invention;

FIG. 2 is a fragmentary, sectional, enlarged view of the IUD remover of FIG. 1;

FIG. 3 is a sectional, enlarged view of the tip of the IUD remover of FIG. 1; and FIG. 4 is a fragmentary, enlarged view of the tip of the IUD remover of FIG. 1 showing the helical groove therein.

DESCRIPTION OF THE PREFERRED EMBODIMENT

In the drawings the preferred embodiment of the IUD remover is generally designated 11. The basic components of remover 11 are: a handle 12, an elongated tube 13, a malleable hollow extension 14 of tube 13, and a filament 15.

Referring to FIG. 2, handle 12 is generally cylindrical and includes a grip portion 16 and an integral shaft 17. Grip portion 16 has approximately the same diameter as the outer diameter of tube 13. Shaft 17 is composed of three integral segments 18, 19, 22 of respectively decreased diameter that are received into end 23 of tube 13 and extend axially thereinto. Each segment 18, 19, 22 has a diameter smaller than the inner diameter of the portion of tube 13 in which it resides, such that shaft 17 is restrictively slidable axially within tube 13. A shoulder 24 of handle 12 at the transition between the grip portion 16 and shaft 17 engages the edge of end 23 of tube 13 when shaft 17 is slid fully into tube 13 and serves as a stop to prevent grip portion 16 from entering tube 13.

Malleable extension 14 is press fit into the opposite end 25 of tube 13. As seen in FIGS. 1 and 2, the exposed portion (that segment not within tube 13) of extension 14 is tapered. A cylindrical tip 26 is press fit into the leading end of extension 14 (FIG. 3). The segment of tip 26 that tends outwardly from extension 14 has the same outer diameter as the leading end of extension 14 so that the transition between extension 14 and tip 26 is smooth. Tip 26 has a central axial bore 27 extending from its end 28 partly through it. It also has a diametrical hole 29 near its leading end 32; a biased radial hole 33 that opens into the leading end of axial bore 27, is generally planar with diametrical hole 29 and whose entrance is diametrically opposite opening 34 of bore 29; and a helical groove (FIG. 4) 30 in its exterior surface that extends from opening 34 of hole 29 to the opening of biased radial hole 33.

End 35 of filament 15 is interference fit within diametrical hole 29 and filament 15 extends outwardly from opening 34 of bore 29, loops around end 32 of tip 26 into radial hole 33, therethrough into bore 27, therethrough into extension 14, and therethrough to segment 22 of shaft 17 of handle 12. The leading end of segment 22 has an axial bore 36 in which end 37 of filament 15 is affixed (FIGS. 2 and 3).

Referring to FIG. 1, filament 15 defines a loop 38 of predetermined size (approximately 10 to 15 mm diameter) that extends outwardly from end 32 of tip 26 when shaft 17 of handle 12 is slid fully within tube 13 (illustrated in solid line in FIG. 1). As illustrated in phantom in FIG. 1 the size of loop 38 may be decreased by gripping grip portion 16 of handle 12 and sliding handle 12 in the direction indicated by the solid arrow. Since end 36 of filament 15 is affixed to handle 12 such sliding pulls the portion of filament 15 that defines loop 38 through hole 33 and rearwardly in the direction of the solid arrow. When handle 12 is slid as far out of tube 13 as it will go, loop 38 has been contracted such that it is engaged snugly within helical groove 30. By sliding handle 12 back (in the direction opposite the solid arrow), loop 38 disengages groove 30 and increases in size until it reaches the size shown in solid line in FIG. 1.

Remover 11 may be used to remove an IUD of the above described type from within a uterus as follows. Loop 38 is pulled snugly into groove 30 by gripping handle 12 at grip portion 16 and sliding handle 12 in the direction of the solid arrow as far as it will go. With filament 15 so positioned the leading end of remover 11 presents a smooth, small surface for penetrating the cervical canal. Malleable extension 14 is then bent so that it conforms generally to the longitudinal configuration of the cervical canal. Remover 11 is then inserted tip 26 first through the vagina and into the cervical canal a short distance via the external cervical os. Loop 36 is then expanded by sliding handle 12 to its forwardmost position. (Shoulder 24 will be flush against end 23 of tube 13). Remover 11 is then slowly rotated about its longitudinal axis back and forth over about a 180° sweep while it is slowly inserted further into the cervical canal. This sweeping increases the likelihood that the longitudinally extending appendage of the IUD will be encircled by loop 38. Once the tip 26 has been inserted about half of the way into the uterus, loop 38 is retracted by sliding handle 12 rearwardly as far as it will go. If the IUD appendage has been encircled by loop 38 such retraction will cause said appendage to be entrapped tightly against tip 26 by loop 38, thus preventing loop 38 from itself being drawn tightly about tip 26. A circumferential mark 42 about segment 18 of shaft 17 serves as indicia whether the IUD appendage has been so entrapped. When mark 42 is aligned with the end 23 of tube 13 the size of loop 38 is approximately the minimal size capable of encircling the IUD appendage. Thus, if the appendage has not been entrapped mark 42 will be rearward of end 23 and quite visible. If such is the case the remover is withdrawn to the external cervical os and the procedure is repeated. Correlatively, if the appendage has been entrapped, mark 42 will be forward of end 23 and not visible. If such is the case the removal of the IUD may be accomplished by withdrawing remover 11 from the cervical canal—with the ensnared IUD being withdrawn out of the uterus and cervical canal along with the remover 11.

Modifications of the above described IUD remover that are obvious to those of skill in the mechanical, medical instrument, and related arts are intended to be within the scope of the following claims.

I claim:

1. Apparatus for removing an intrauterine device from a uterus via the cervical canal comprising:
   a. a rod-shaped handle;
   b. a hollow elongated tube, one end of which fits over one end of the handle such that the handle is slidable axailly within the tube from a first position to a second position;
   c. a hole through the side of the hollow tube at the other end of the hollow tube; and
   d. a filament extending from said other end of the tube through the hole to the said one end of the handle, one end of the filament being attached to the side of the hollow tube at a position above and generally opposite the hole and the other end of the filament being attached to said one end of the handle, the filament being wrapped about said other end of the tube when the handle is in said first position and defining a loop of predetermined size that extends outwardly from said other end of the hollow tube when the handle is in its second position, the size of said loop being adjustable by sliding the handle between said first and second positions.

2. The apparatus of claim 1 wherein the handle includes stop means that engages said one end of the tube when the handle is in said first position to prevent the handle from being slid further into the tube.

3. The apparatus of claim 2 wherein the stop means is a segment of the handle having a diameter larger than the inner diameter of the tube.

4. The apparatus of claim 1 wherein the leading portion of the hollow tube is malleable, whereby such leading portion may be bent to facilitate the insertion of the apparatus through the cervical canal.

5. The apparatus of claim 1 including (e) a generally helical groove in the exterior of the tube that extends from the position of attachment of the filament to the tube to the hole, said groove receiving the filament when the filament is wrapped about said other end of the tube by sliding the handle to said first position.

6. The apparatus of claim 1 including:
   e. a mark on the segment of the handle that slides within the tube, the mark being indicia of the size of the loop.

7. The apparatus of claim 1 wherein the leading portion of the tube is tapered to facilitate the insertion of the apparatus through the cervical canal.

8. The apparatus of claim 5 including:
   f. a mark on the segment of the handle that slides within the tube, the mark being indicia of the size of the loop; and
   g. wherein the handle has a segment of greater diameter than the inner diameter of the tube that engages said one end of the tube when the handle is in said first position to prevent the handle from being slid further into the tube; and the leading portion of the tube is malleable and tapered.

* * * * *